US010383597B2

(12) United States Patent
Yukov

(10) Patent No.: US 10,383,597 B2
(45) Date of Patent: Aug. 20, 2019

(54) YUKOV TISSUE CHARACTERIZATION METHOD AND APPARATUS

(71) Applicant: Igor Yukov, Orange, CT (US)

(72) Inventor: Igor Yukov, Orange, CT (US)

( * ) Notice: Subject to any disclaimer, the term of this patent is extended or adjusted under 35 U.S.C. 154(b) by 0 days.

(21) Appl. No.: 15/732,780

(22) Filed: Dec. 29, 2017

(65) Prior Publication Data

US 2018/0185006 A1    Jul. 5, 2018

Related U.S. Application Data

(63) Continuation-in-part of application No. 14/998,914, filed on Mar. 4, 2016, now abandoned.

(51) Int. Cl.
*A61B 8/14* (2006.01)
*A61B 8/08* (2006.01)
*A61B 8/00* (2006.01)

(52) U.S. Cl.
CPC .............. *A61B 8/145* (2013.01); *A61B 8/08* (2013.01); *A61B 8/4416* (2013.01);
(Continued)

(58) Field of Classification Search
CPC ......... A61B 8/145; A61B 8/08; A61B 8/4416; A61B 8/4488; A61B 8/463; A61B 8/469; A61B 8/5246

See application file for complete search history.

(56) References Cited

U.S. PATENT DOCUMENTS 4,228,804 A * 10/1980 Holasek .............. G01S 7/52036
600/443
4,932,414 A * 6/1990 Coleman .................. A61B 8/14
128/916

(Continued)

FOREIGN PATENT DOCUMENTS

CN          1249164     *   4/2000
CN          1113631 C       7/2003

*Primary Examiner* — Matthew F Desanto
(74) *Attorney, Agent, or Firm* — Ingerium Patents LLC; Peter R. Kramer

(57) ABSTRACT

An apparatus for improving the quality of the existing ultrasound diagnostic examination by non-invasively determining a type of tissue matter within a living entity consisting of application of two different ultrasound diagnostic methods simultaneously, in a sequence or alternate through the same transducer is disclosed. The apparatus uses a B-scan tissue image visualization as a guiding image to apply a tissue characterization method to determine an attenuation data for tissue matter and includes the steps of applying arbitrary waveform generator to produce a B-scan image of the tissue matter to be analyzed, selecting a region of interest on said image, detecting reflected signals from said region of interest, analyzing the reflected signals to determine attenuation data for the tissue matter. The same advanced combined diagnostic examination can be achieved by using any existing on the market ultrasound diagnostic apparatus with a B-scan transducer by using interface adapter-switch consisting of switching of some piezo-elements of said B-scan transducer to the tissue characterization method for the period of application of said tissue characterization apparatus to determine a type of the tissue matter being under examination within a living entity.

1 Claim, 2 Drawing Sheets

(52) U.S. Cl.
CPC .......... *A61B 8/5223* (2013.01); *A61B 8/5246* (2013.01); *A61B 8/4488* (2013.01); *A61B 8/463* (2013.01); *A61B 8/469* (2013.01); *A61B 8/5269* (2013.01); *A61B 8/56* (2013.01)

(56) References Cited

U.S. PATENT DOCUMENTS

| | | | | |
|---|---|---|---|---|
| 5,361,767 | A | * | 11/1994 | Yukov .................. A61B 8/0858 600/442 |
| 6,007,489 | A | | 12/1999 | Yost |
| 6,511,427 | B1 | * | 1/2003 | Sliwa, Jr. ............. A61B 5/4869 600/438 |
| 7,698,142 | B2 | * | 4/2010 | Washburn ................ A61B 8/13 704/231 |
| 2014/0350403 | A1 | * | 11/2014 | Kho ....................... A61B 8/483 600/442 |
| 2015/0141822 | A1 | * | 5/2015 | Miyauchi .............. G06T 7/0012 600/438 |
| 2017/0119352 | A1 | * | 5/2017 | Anand ...................... G06T 7/11 |
| 2018/0055479 | A1 | * | 3/2018 | Lalena ............... G01S 7/52098 |

* cited by examiner

YUKOV TISSUE CHARACTERIZATION METHOD AND APPARATUS

BACKGROUND OF THE INVENTION

The present invention relates to improvement of the quality of existing ultrasound diagnostic examination by combining a B-scan visualization technique with a Two-Frequency Attenuation Method technique to obtain high quality ultrasound diagnostic examination including non-invasive determination the type of the issue matter under ultrasound investigation.

For many years specialists in ultrasound diagnostic field trying to develop an ultrasound diagnostic method and apparatus which can provide information to differentiate type of tissue through measuring attenuation data in a living body or by finding a pattern of the tissue images. There are many attempts to reach that goal by using spectrum analyzes of reflected signals like U.S. Pat. No. 6,007,489 to Yost et al., European Patent No. 11840135 to Hironaka and many others that could not come up with an objective and reliable method for clinical applications. Some specialists like European Patent No. PCT/IB2014/067105 to Schneider, European Pat. No. PCT/CA2014/2014/050480 to Sadeghi, U.S. patent Ser. No. 14/096,960 to Anuja, European Pat. No. PCT/US2014/011631 to Chen and others tried to find a pattern in a tissue images to differentiate the type of tissue. All attempts to find some positive information to improve B-scan visualization examination to differentiate type of tissue was not successful since reflected echo-signals depend not only on attenuation information from inside of the tissue structure but also on the angle of incident of the ultrasound pulses to reflected surface, its geometry and roughness. Attempts to find a system employing ultrasound methods for determination the nature of tissue within a living body is still continuing. One such system is disclosed in U.S. Pat. No. 5,361,767 to Yukov. This system determines a type of tissue by using methods and apparatuses for a "Two-Frequency Method" of tissue characterization which is based on applying two different frequencies and by registering reflected signals to calculate a differential attenuation coefficient of the tissue through formula:

$$a(f2)-a(f1)=[A1(f2)/A2(f2)-A1(f1)/A2(f1)]/2\ 1\ dB/Cm/MHz,$$

where $a(f1)$ and $a(f2)$—attenuation coefficient on frequencies f1 and f2 accordingly; $A1$ (f1), $A2(f1)$ and $A1(f2)$, $A2(f2)$ are amplitudes of the reflected signals from front and rare boundaries of a layer on frequencies f1 and f2 accordingly; l—is a thickness of a layer.

Author describes requirements for the reflected signals to be processed through mathematical algorithm since as mentioned there is no direct dependency between reflected signals and attenuation information. For that purpose, author suggests obtaining objective information related to attenuation data through analyses of the shape, width and registered time of reflected signals on applied two different frequencies. Chinese Patent No. CN1113631C to Korotkoff discloses a two-frequency method and apparatus which is based on a developed "Two-Frequency Method" described in U.S. Pat. No. 5,361,767. Author suggests subtraction of reflected signals automatically on two different frequencies and displaying the results as a two-dimensional attenuation image on the screen. As mentioned since there is no direct dependency between reflected signals and attenuation information the apparatus in Chinese Pat. No. CN1113631C for automatic two-dimensional attenuation image display cannot obtain objective attenuation information and it will. be impossible to apply in the clinical environment as an objective diagnostic method.

U.S. Pat. No. 5,361,767 to Yukov suggests using the Two-Frequency Method as a Tissue Characterization Method together with a B-scan tissue structure image information, which makes it easier to find a spot of interest for measurement of attenuation. This reference also suggests using the same B-scan transducer simultaneously, in sequence or alternately as a B-scan image visualization method and as a transducer for a Two-Frequency Attenuation Method in order to calculate attenuation data from a spot of interest for generating tissue characterization information. Yukov did not mention that there are fundamental differences between the requirements for B-scan transducers and Two-Frequency Attenuation Method transducers. B-scan transducers require different types of excitation pulses which must be very sharp and short to achieve high resolution of tissue structure image. In contrast, the excitation pulse for a Two-Frequency Method transducer consist of several sine-waves.

Another big difference is that a B-scan transducer requires multiple piezo-elements but a Two-Frequency Method transducer requires only one piezo-element (i.e., only one emitter-receiver source). Because of these differences there are limitations for applying a regular B-scan transducer for both methods. Very sharp and short excitation pulses of a B-scan imaging system produces a very high resolution of the tissue structure images. However, in many cases there is still not enough information to differentiate the type of abnormalities in the patient's body. B-scan imaging systems need some extra information to resolve this problem. One type of needed information would account for different attenuation values according to the type of tissue.

Applying B-scan image visualization combined with a Two-Frequency Attenuation Method for tissue characterization can improve quality of the ultrasound diagnostic examinations and will make it possible to determine types of the tissue non-invasively in a living entity.

SUMMARY OF THE INVENTION

It is an object of the present invention to improve the quality of the existing diagnostic examination by providing an apparatus which combines the application of a B-scan image visualization method and a tissue characterization method where a B-scan image is used as a guiding image apply the two-frequency tissue characterization method to overcome the aforementioned problems.

It is a further object of the present invention to improve the quality of ultrasound diagnostic examination by adapting existing instrumentation to combine the application of B-scan visualization method and tissue characterization method. A B-scan transducer can be adapted to function as two separate transducers for both methods in a sequence or alternate thereby enabling medical specialists to conveniently apply B-scan image information as a guiding image to use with the tissue characterization method for accurate determination of tissue types when performing ultrasound imaging procedures.

It is still a further object of the present invention to provide a reliable interface adapter for use with existing B-scan imaging apparatuses which would permit applying in a sequence or alternately use of the existing B-scan apparatus with a tissue characterization apparatus (i.e., transducer). By using a reliable interface adapter-switch or by placing the bodies of the physically and electrically separate transducers next to each other accurate determination of tissue types can be achieved during examination.

These and other objects and advantages will become more apparent from the following description and drawings.

In accordance with the present invention the improved quality of the existing ultrasound diagnostic examination broadly comprises the steps of: applying a B-scan transducer for visualization of a B-scan tissue imaging and using said B-scan transducer simultaneously for a tissue characterization imaging; placing said B-scan transducer on a patient's body; displaying B-scan tissue images on a monitor; analyzing said B-scan tissue images; selecting a region of interest on said displayed B-scan images on said monitor; displaying A-mode signals on the screen next to the displayed said B-scan images on said monitor; automatically processing or visually analyzing said A-mode signals from said chosen region displayed on said monitor next to displayed said B-scan image, thereby obtaining objective attenuation data to determine a type of tissue being under investigation.

The apparatus for improved quality of the existing ultrasound diagnostic examination can be performed also by using B-scan imaging apparatus with a B-scan transducer and by electronically connecting inside of the B-scan transducer a group of chosen piezo-elements to function as an A-mode transducer and to apply said A-mode transducer for tissue characterization method in a sequence or alternate and use said B-scan images as a guiding image for application of said tissue characterization method to determine type of tissue being under investigation.

The apparatus for the improved quality of the existing ultrasound diagnostic examination also can be performed by using existing on the market any B-scan apparatus with a B-scan transducer and by electronically connecting chosen piezo-elements inside of the B-scan transducer as a single A-mode transducer through a reliable interface adapter-switch to apply tissue characterization apparatus or by placing next to each other the B-scan transducer and an A-mode transducer of the tissue characterization apparatus and to apply in a sequence or alternate said B-scan apparatus and said tissue characterization apparatus and to use said B-scan image as a guiding image to apply said tissue characterization method to determine type of the tissue being under investigation.

Details of the apparatus of present invention which is to improve quality of the existing ultrasound diagnostic examination are set forth in the following detailed description and the accompanying drawings wherein like reference numerals depict like elements.

DETAILED DESCRIPTION OF THE INVENTION

Figure 1:
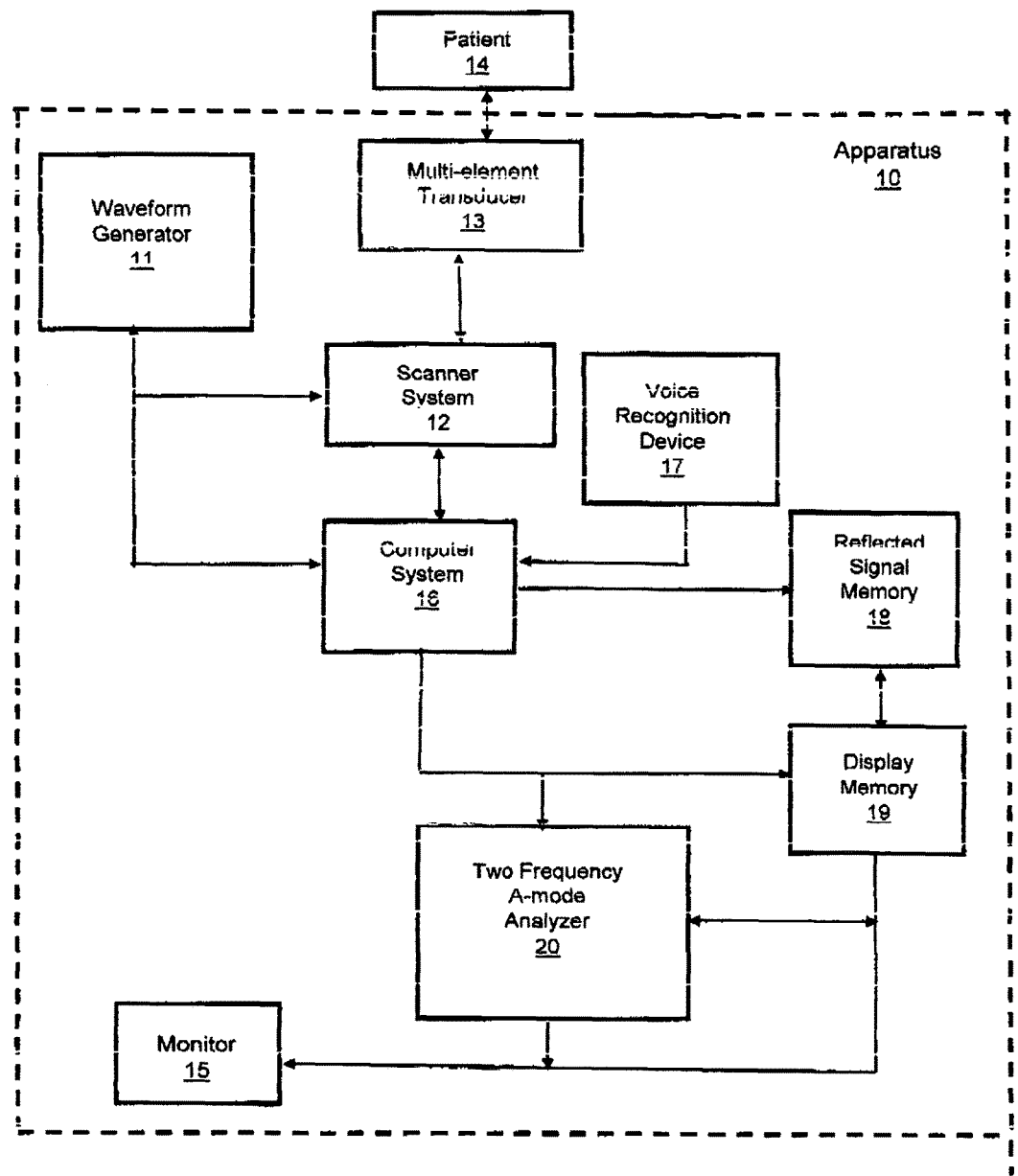
FIG. 1 is a schematic representation of a combined apparatus which can perform simultaneous application of B-scan imaging method and Tissue Characterization method.

Referring now to the drawings, FIG. 1 illustrates a combined apparatus functioning simultaneously as a B-scan imaging method and as a Tissue Characterization method with one B-scan transducer for both said methods which is the object of the present invention.

The combined apparatus of B-scan imaging method and Tissue Characterization method designed based on the technical requirements for the Two-Frequency Attenuation Method which is the Tissue Characterization Method.

In one aspect of the invention each piezo-element of a B-scan transducer must function separately and independently as an A-mode transducer. The excitation pulses from a waveform generator must be comprised of several sinewaves for each chosen frequency of two different frequencies applied in a sequence and the pulses must separately excite each of the independently functioning piezo-elements of the B-scan transducer. By connecting independently functioning piezo elements of a B-scan transducer to a linear scanning system a B-scan image of a tissue is created with simultaneous application the same reflected signals as A-mode signals thereby permitting calculation of attenuation data.

The apparatus 10 as shown on FIG. 1 includes means 11 an arbitrary a waveform generator 11 for generating pulses as desired at two different frequencies with desired width and shape. The apparatus 10 further includes a linear scanning system 12 with a multi piezo-element B-scan transducer 13 constructed in accordance with the technical requirements of the Two-Frequency Method for tissue characterization. Each piezo-element of said B-scan transducer 13 emits and receives signals on two different chosen frequencies having a certain width and shape from the waveform generator 11. An operator can place the multi piezo-elements B-scan transducer 13 on the surface of the body of a patient 14 and display in a sequence two B-scan images on two different frequencies for visualization on a monitor 15 by using computer system 16 with a program memory and control systems that are available on the market having all the features necessary for examination and analyzes of the B-scan images so that the B-scan images can be displayed in a sequence or individually by choice. On the screen of monitor 15 an operator can analyze any spot of interest on the B-scan images by applying the tissue characterization method to determine the attenuation data for the spot of interest in the tissue under examination. Analysis of the A-mode signals from the chosen spot and calculation of the attenuation data from the chosen spot can be processed automatically and displayed as an overlay on the chosen spot on the screen displaying the B-scan images. A living body consists of different types of tissues having layers and boundaries. A B-scan imaging method displays the structure of the tissue layers and their boundaries. In many cases this information is not enough to differentiate the type of tissue. The tissue characterization apparatus can differentiate the type of tissue but only through reflected signals from boundaries of the layers because existing technology does not have enough accuracy to measure attenuation in the tiny structures of the tissue. The tissue characterization method requires two reflected signals to calculate the attenuation data between the reflected signals: one reflected signal from front boundary of the layer and a second reflected signal from the rear boundary of the layer. The B-scan transducer 13 as described above consists of multiple piezo-elements which function independently for B-scan imaging and for simultaneous tissue characterization according to the two-frequency method. The operator must know that each piezo-element has its own image display. To measure attenuation in a spot of interest found through B-scan image requires finding two reflected signals coming from the same piezo-element. The operator must click on a chosen reflected signal on the B-scan image and a line will appear to show the direction of the reflected signals coming from the piezo-element. The operator must find and click on the second reflected signal from the piezo-element and it should be a rear boundary of the chosen layer. The attenuation data will be displayed by choice on the B-scan image screen as an overlaid color image or as numerical data between the chosen reflected signals or displayed as numerical data on a smaller screen next to the B-scan image display on the monitor 15. If needed the operator can see and analyze the reflected signals from the corresponding piezo-element as A-mode signals which can be displayed on the screen of the monitor 15 next to the B-scan image displays. On the top of the B-scan imaging screen of the monitor 15 there are numbers corresponding to each piezo-element of the B-scan transducer 13. By clicking the number an operator can activate the direction line of the piezo-element. The operator also can use a Voice Recognition block 17 to activate the direction line of any piezo-element by pronouncing a number to find a corresponding piezo-element. The operator also can use A-mode Analyzer block 20 to make analyses of said A-mode signals automatically. The display of B-scan tissue images simultaneously with overlaid said tissue characterization information will greatly improve the quality of ultrasound diagnostic examinations.

In accordance with the present invention the combined method of B-scan imaging with the two-frequency tissue characterization can also be accomplished by using a regular high resolution B-scan apparatus having multi piezo-elements B-scan transducer connected to any type of scanning system.

A row of A-mode transducers is connected to a separate linear scanning system and waveform generator. The row of A-mode transducers is disposed within a B-scan transducer wherein the B-scan transducer is comprised of multi-piezo elements. The waveform generator produces pulses of two different frequencies which can be applied for an appropriate time to the row of A-mode transducers in a sequence or alternately by means of switches thereby enabling incorporation the two-frequency tissue characterization method with B-scan imaging.

To effectuate a configuration of A-mode transducers within an existing B-scan transducer, wherein the B-scan transducer is comprised of multi-piezo elements, it is required to form a row of piezo-elements by connecting a group of adjacent piezo-elements together using switches and to use this group of connected piezo-elements as one A-mode transducer for tissue characterization. By creating a row of A-mode transducers along the length of the multi piezo-elements of the B-scan transducer the B-scan transducer can be applied for B-scan imaging and tissue characterization imaging wherein a B-scan image can be used as a guiding image for applying the tissue characterization method thereby improving the quality of existing ultrasound diagnostic examination instrumentation. This combined apparatus shares many functionalities described in the combined apparatus of FIG. 1

In accordance with the present invention any existing multi-piezo element B-scan transducer currently available on the market can be adapted for B-scan examination with two-frequency tissue characterization essentially as described above by using a novel interface adapter switch. By means of the adapter switch a single A-mode transducer is effectively provided as described below.

Figure 2:
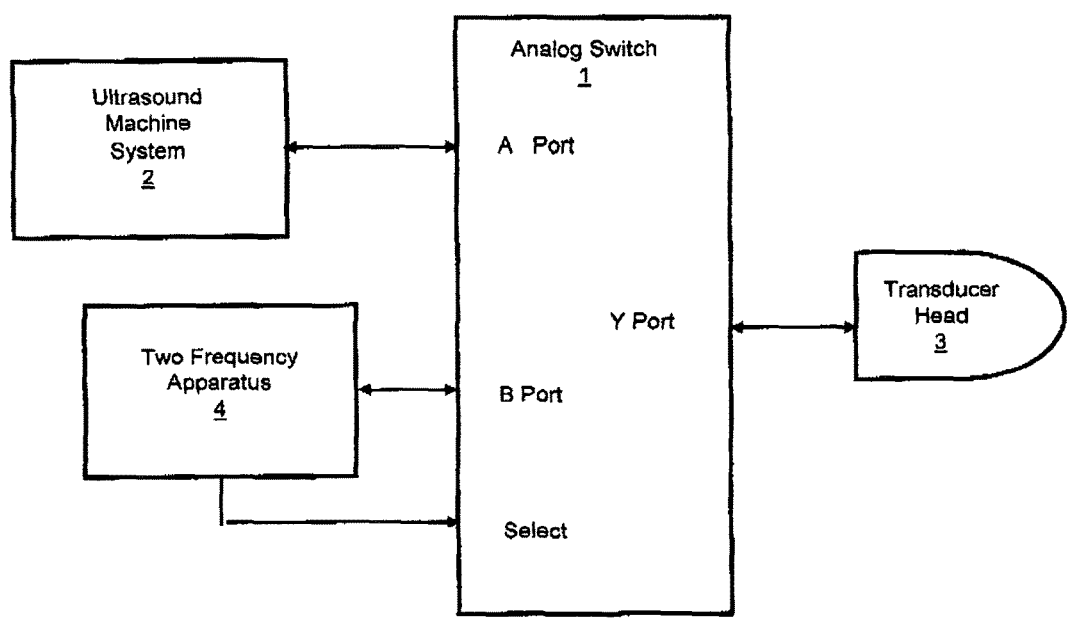
FIG. 2 is a schematic representation of the interface adapter-switch to apply B-scan imaging apparatus and a tissue characterization apparatus through B-scan transducer.

FIG. 2 illustrate a block diagram of an interface adapter-switch which can connect together some of the piezo-elements of a B-scan transducer to make a connected group of piezo-elements as an A-mode transducer for two-frequency tissue characterization. The adapter-switch illustrated in FIG. 2 works through a TTL logic level signal via Analog Switch 1. When it is driven with a logic "1" the System 2 of the ultrasound apparatus is connected to the transducer Head 3. Also, it is "pulled up", when nothing is connected to the input, the ultrasound apparatus System 2 is connected to the transducer Head 3. When it is driven with a logic "0" (or shorted to ground) all elements are disconnected from the ultrasound apparatus System 2 and the "IN" signal from tissue characterization apparatus 4 through B-port of said Analog Switch 1 is connected to the central elements of the transducer Head 3. A high voltage switch IC can be used for a relay which provides switching of the center chosen amount of piezo-elements between a B-scan apparatus and a Tissue Characterization apparatus. The remaining amount of piezo-elements have a single switch for each piezo-element so that all piezo-elements of the B-scan transducer see the same impedance when driven by the B-scan apparatus. These switches are opened by disconnecting the B-scan apparatus's system from the transducer when the external transceiver is connected to the center chosen amount of piezo-elements.

In accordance with the present invention the combined application of a B-scan imaging method and a Tissue Characterization method can be provided also by using any commercially available B-scan apparatus with any type of B-scan transducer and a tissue characterization apparatus with A-mode transducer and by placing the B-scan transducer and the A-mode transducer together next to each other as one combined transducer. By applying the B-scan apparatus and tissue characterization apparatus separately but in a sequence or alternately through, for instance a Foot Pedal switch, an operator can visualize a B-scan image of the tissue being under investigation and to use said B-scan image as a guiding image to choose a spot of interest. After selecting a spot of interest the operator can slide the combined transducer to bring the A-mode transducer component to the spot of interest for characterization by the two-frequency method essentially described above.

It is apparent that there has been provided in accordance with this invention devices and methods for non-invasively determining a type of tissue within a living entity which fully satisfies the objects, means and advantages set forth herein-before. While the invention has been described in combination with specific embodiment thereof, it is evident that many alternatives, modifications and variations will be apparent to those skilled in the art in light of the foregoing description. Accordingly, it intended to embrace all such alternatives, modifications and variations as fall within the spirit and broad scope of the appended claims.

I claim:

1. A tissue characterization method which applies B-scan visualization and two-frequency attenuation for characterization of a tissue in a patient comprising the following steps:

(a) providing a B-scan apparatus wherein said B-scan apparatus has a B-scan transducer, said B-scan transducer comprised of a plurality of piezo-elements, a scanning system and a pulse generator, (b) providing a two-frequency attenuation apparatus, said two frequency attenuation apparatus has a row of A-mode transducers inside said B-scan transducer and connected to a separate linear scanning system and waveform generator and which is configured to function through a subset of said plurality of piezo-elements of said B-scan transducer, said two frequency apparatus configured to generate sinusoidal ultrasound excitation pulses for said A-mode transducers, said sinusoidal excitation pulses comprising pulses of two different frequencies, (c) placing the B-scan transducer on the patient's body, (d) displaying on the monitor a B-scan image of the patient's tissue, (e) selecting a spot of interest on said B-scan image displayed on the screen of said monitor, (f) using a foot pedal to activate connection of said subset of said plurality of piezo-elements by means of switches in order to work as a single A-mode transducer for tissue characterization, (g) sliding said B-scan transducer on said patient's body to bring said A-mode transducers to said selected spot of interest, and scanning said selected spot of interest with said A-mode transducers, (h) displaying on the screen of said monitor next to display of said B-scan images the A-mode images on chosen said two different frequencies from said selected spot of interest, (i) analyzing the A-mode images either visually or with an analyzer, amplitudes, shapes, widths and registered times of reflected signals on said chosen two different frequencies from said selected spot of interest to obtain data for a differential attenuation coefficient, thereby permitting differentiation between types of tissue within an organ through analysis of reflected signals from boundaries of tissue layers, (j) displaying said obtained data for said differential attenuation coefficient on the B-scan image as an overlay color image or as numerical data thereby permitting determination of the type of tissue matter from said selected spot of interest.

\* \* \* \* \*